United States Patent [19]

Stephen et al.

[11] Patent Number: 4,600,740

[45] Date of Patent: Jul. 15, 1986

[54] HINDERED DYDROXYBENZYL HEXAALKYLDIPHENYL-METHANES AND STABILIZED COMPOSITIONS

[75] Inventors: John F. Stephen, West Chester, Pa.; Jerry H. Smith; Makram H. Meshreki, both of Wilmington, Del.

[73] Assignee: ICI Americas Inc., Wilmington, Del.

[21] Appl. No.: 765,671

[22] Filed: Aug. 15, 1985

[51] Int. Cl.[4] .......................... C07C 39/12; C08K 5/13
[52] U.S. Cl. .................................... 524/120; 524/127; 524/151; 524/289; 524/304; 524/342; 568/720
[58] Field of Search ............... 524/342, 304, 120, 127, 524/151, 289; 568/720; 528/219

[56] References Cited

U.S. PATENT DOCUMENTS 3,026,264  3/1962  Rocklin et al. ............... 568/720
3,105,767  10/1963  Arabian ............................ 568/720

Primary Examiner—Veronica P. Hoke
Attorney, Agent, or Firm—Richard A. Rowe

[57] ABSTRACT

Novel hydroxybenzyl substituted hexaalkyldiphenylmethane derivatives are provided which are useful as stabilizers of resins made from at least one ethylenically unsaturated monomer.

5 Claims, No Drawings

HINDERED DYDROXYBENZYL HEXAALKYLDIPHENYL-METHANES AND STABILIZED COMPOSITIONS

The present invention relates to novel hindered hydroxybenzyl hexaalkyldiphenylmethanes and to stabilized polymer resins containing these materials. It also relates to resins containing the novel stabilizers with costabilizers including thiosynergists and phosphites.

The hindered hydroxybenzyl derivatives of the invention have the following general formula:

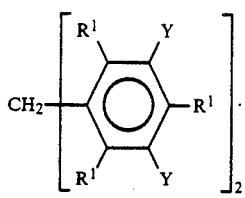

wherein: Y is

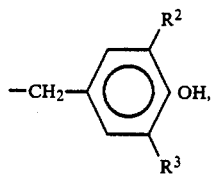

$R^1$ groups are alkyl having 1 to 8 carbon atoms, and $R^2$ and $R^3$ are independently alkyl groups having 1 to 8 carbon atoms. Preferably, $R^1$ groups are lower alkyl having 1 to 4 carbon atoms and $R^2$ and $R^3$ are alkyl groups having 3 to 8 carbon atoms and branched at the α-carbon atom. Most preferably, $R^1$ is methyl and $R^2$ and $R^3$ are tert-butyl.

European Pat. No. 0,047,649, U.S. Pat. Nos. 3,026,264, 3,925,488 and German OLS No. 1,910,793 describe the use of trishydroxybenzyl derivatives of mesitylene as antioxidants and stabilizers for polymer resins.

The compounds of the instant invention are unexpectedly superior to those of the prior art.

Compounds of the invention can be prepared by reaction of a substituted hydroxybenzyl compound of the following general formula with a diarylmethane in the presence of a catalyst:

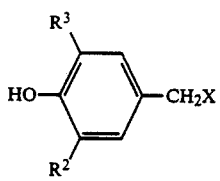

wherein $R^2$ and $R^3$ are alkyl groups having 1 to 8 carbon atoms and wherein X is selected from hydroxyl, halogen, alkoxy, secondary alkamino, and alkylcarboxy wherein the alkyl group has from 1 to 8 carbon atoms. Methods for preparing these substituted hydroxybenzyl compounds have been described in: F. S. Granger, "Industrial and Engineering Chemistry," 24, 442 (1932); U.S. Pat. No. 3,030,428; M. S. Kharasch and B. S. Joshi, J. Org. Chem., 22, 1435 (1957); and WO84/02336. The diarylmethanes can be prepared from substituted benzene compounds and formaldehyde by methods known in the art such as C. M. Welch and H. A. Smith, J. Am. Chem. Soc., 73, 4391 (1951); "Organic Syntheses," col. vol. 5, 422 (1973) and U.S. Pat. No. 2,981,765. Catalysts and general procedures for hydroxybenzylation reactions are disclosed in U.S. Pat. Nos. 3,026,264, 3,925,488, 4,259,534, and 4,340,767. The reaction may be carried out in the presence of acidic catalyst such as sulfuric acid and p-toluene sulfonic acid.

The compounds of the invention are stabilizers of organic materials normally subject to thermal and oxidative deterioration. Material which are thus stabilized include synthetic organic polymeric substances such as vinyl resins formed from the polymerization of vinyl halides or from the copolymerization of vinyl halides with unsaturated polymerizable compounds, e.g., vinylesters, α,β-unsaturated ketones, α,β-unsaturated aldehydes, and unsaturated hydrocarbons such as butadiene and styrene; poly-α-olefins such as polyethylene, polypropylene, polybutylene, and the like, including copolymers of poly-α-olefins, polyurethanes and polyamides such as polyhexamethylene adipamide and polycaprolactam; polyesters such as polyethylene terephthalate; polycarbonates; polyacetals; polystyrene; polyethyleneoxide; polyisoprene; polybutadiene and copolymer such as those of high impact polystyrene containing copolymers of butadiene and styrene and those formed by the copolymerization of acrylonitrile, butadiene and/or styrene.

In general, one or more of the stabilizers of the present invention are employed in an amount ranging from about 0.005 to about 5% by weight of the composition to be stabilized. A particularly advantageous range of the present stabilizers is from about 0.05 to about 2%. The preferred range is particularly effective in polyolefins such as polypropylene.

These compounds may be incorporated in the polymer substance during the usual processing operations, for example, by milling or extrusion. The stabilized polymer can be fabricated into films, fibers, filaments, hollow-spheres and the like. The heat stabilized properties of these compounds advantageously stabilize the polymer against degradation during such processing at the high temperatures generally encountered.

The stabilizers employed in this invention can also be used in combination with other stabilizers or additives. Especially useful co-stabilizers are dilauryl-β-thiodipropionate and distearyl-β-thiodipropionate.

The stabilizers described in this invention can be used in combination with di- and tri-alkyl and alkyl phenyl phosphites such as tris-nonylphenyl phosphite, tris di-tert-butyl phenyl phosphite, bis(2,4-di-t-butyl phenyl)-pentaerythritol diphosphite, tetra(di-tert-butyl phenyl)-diphenyl-4,4'-ene-diphosphonite, and distearyl pentaerythritol diphosphite.

Other antioxidants, antiozonants, thermal stabilizers, ultraviolet light absorbers, coloring materials, dyes, pigments, metal chelating agents, etc., may also be used in the compositions in combination with the stabilizers of the invention.

EXAMPLE 1

Methylene bis 2,4,6-trimethyl-3,5-bis(3,5-di-tert-butyl-4-hydroxybenzyl)benzene

Methylene bismesitylene (7.6 g) and methylene chloride (100 ml) were added to a flask equipped with a stirrer, thermometer, reflux condenser and two addition funnels. The mixture was cooled to 0° with stirring. To this mixture were added simultaneously sulfuric acid (14.7 g) and 2,6-di-tert-butyl-4-methoxymethylphenol (37.5 g in 150 ml methylene chloride) over a period of 30–40 minutes while maintaining the temperature at 0°–3° C. After mixing for 30 minutes the reaction mixture was neutralized with an aqueous sodium hydroxide solution and washed with water. The material was obtained from the organic layer and crystallized from heptane to give 24.6 g (73%) of the desired product, m.p. 239°–241° C.

Analysis: Calculated for $C_{79}H_{112}O_4$: C, 84.24; H, 10.02; Found: C, 83.95; H, 10.29.

EXAMPLE 2

This example shows the usefulness of the invention for stabilization of polypropylene. The stabilizers were incorporated into Profax 6301 TM polypropylene resin by solvent blending (methylene chloride) followed by extrusion at 200° C. Twenty-five mil plaques were prepared by compression molding at 6,000 psi and 188° C. Samples were tested in a forced draft oven at 150° C. Failure was determined when the first signs of decomposition were observed. Tests were run in quadruplicate and an average value was determined. Results are shown in Table I.

TABLE I

| Stabilizer | Concentration (%) | Hours to Failure |
|---|---|---|
| none | — | 24 |
| Example 1 | 0.10 | 456 |
| Example 1/DSTDP | 0.10/0.25 | 1500 |

EXAMPLE 3

This example shows the usefulness of the invention for stabilization of high impact polystyrene. The stabilizers were incorporated into high impact polystyrene by milling at 188° C. Twenty mil plaques were prepared by compression molding at 6000 psi and 188° C. Samples were tested in a forced draft oven at 90° C. Failure was determined when cracking was observed after flexing the plaque over a one-inch mandrel. Tests were run in quadruplicate and an average value was determined. Results are shown in Table II.

TABLE II

| Stabilizer | Concentration (%) | Hours to Failure |
|---|---|---|
| none | — | 48 |
| Example 1 | 0.10 | 324 |

EXAMPLE 4

This example shows the usefulness of the invention as a process stabilizer for polypropylene. The stabilizers were incorporated into Profax 6301 TM polypropylene resin by solvent blending (methylene chloride) followed by extrusion at 200° C. The materials were then evaluated for their melt (process) stability according to ASTM standard test method D-1238. Results are shown in Table III.

TABLE III

| Stabilizer | Concentration (%) | Melt Flow Index (g/10 min.) No. or Extrusions | | |
|---|---|---|---|---|
| | | 1 | 3 | 5 |
| none | — | 18.1 | 30.7 | 40.7 |
| Example 1 | .10 | 11.5 | 13.9 | 14.7 |
| Example 1/DSTDP | .10/.25 | 11.3 | 14.0 | 14.0 |
| Example 1/ Weston 618 | .10/.25 | 11.1 | 12.2 | 12.7 |

What is claimed is:

1. A compound of the general formula:

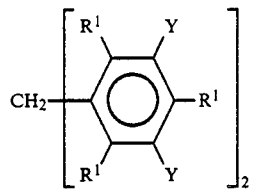

where Y is

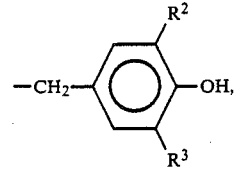

and wherein $R^1$ groups are alkyl having 1 to 8 carbon atoms and $R^2$ and $R^3$ are alkyl groups of 1 to 8 carbon atoms.

2. A compound of claim 1 wherein $R^1$ is —CH₃, and $R^2$ and $R^3$ are tert-butyl.

3. A composition comprising a polymer derived from an ethylenically unsaturated monomer and 0.005–5% by weight of a compound of claim 1.

4. A composition of claim 3 wherein said polymer is selected from the group consisting of polyethylene, polypropylene and polystyrene.

5. A composition of claim 4 further comprising a costabilizer compound selected from the group consisting of dilauryl-β-thiodipropionate, distearyl-β-thiodipropionate, distearylpentaerythritol diphosphite, pentaerythritol tetrakis(3-(dodecylthio)propionate), tris(2,4-di-tert-butylphenyl)phosphite, and bis(2,4-di-tert-butylphenyl)pentaerythritol diphosphate.

* * * * *